United States Patent [19]

Ginsburg

[11] Patent Number: 5,500,699
[45] Date of Patent: Mar. 19, 1996

[54] SPATIAL FREQUENCY AND CONTRAST SENSITIVITY TEST CHART AND PROTOCOL

[76] Inventor: Arthur P. Ginsburg, 130 Ryan Industrial Ct., #105, San Ramon, Calif. 94583

[21] Appl. No.: 400,913

[22] Filed: Mar. 8, 1995

Related U.S. Application Data

[62] Division of Ser. No. 628,786, Dec. 17, 1990, Pat. No. 5,414,479.

[51] Int. Cl.⁶ ......................................................... A61B 3/02
[52] U.S. Cl. ............................ 351/239; 351/243; 351/246
[58] Field of Search ...................................... 351/239, 243, 351/246, 222

[56] References Cited

U.S. PATENT DOCUMENTS 4,365,873  12/1982  Ginsburg .................................. 351/239

*Primary Examiner*—William L. Sikes
*Assistant Examiner*—Hung Xuan Dang
*Attorney, Agent, or Firm*—Townsend and Townsend and Crew

[57] ABSTRACT

A method and apparatus for measuring and quantifying generalized visual sensitivity in terms of contrast sensitivity, spatial frequency response and eye brain recognition of image alignments or shapes is disclosed. A multiplicity of distinctly different information areas are provided, each of these information areas being generally delineated by indicia so as to eliminate patient or system search for an image and to generally designate the proximity of the information area for visual interrogation. The information areas may contain a grating having successive parallel aligned light and dark areas, which parallel aligned light and dark areas have a substantially linear character with the contrast levels and/or spatial frequency or size of occurrence differing for different information areas. Each successive information area has a background with mean luminance being the average of that mean luminance found within the information area. Further, all information areas are provided with a taper at their edges, preferably a Gaussian taper, which taper imparts to the edges boundaries that blend into the mean luminance background. There results for images on the threshold of visual acuity information areas which only with careful examination can be discriminated from their backgrounds.

2 Claims, 4 Drawing Sheets

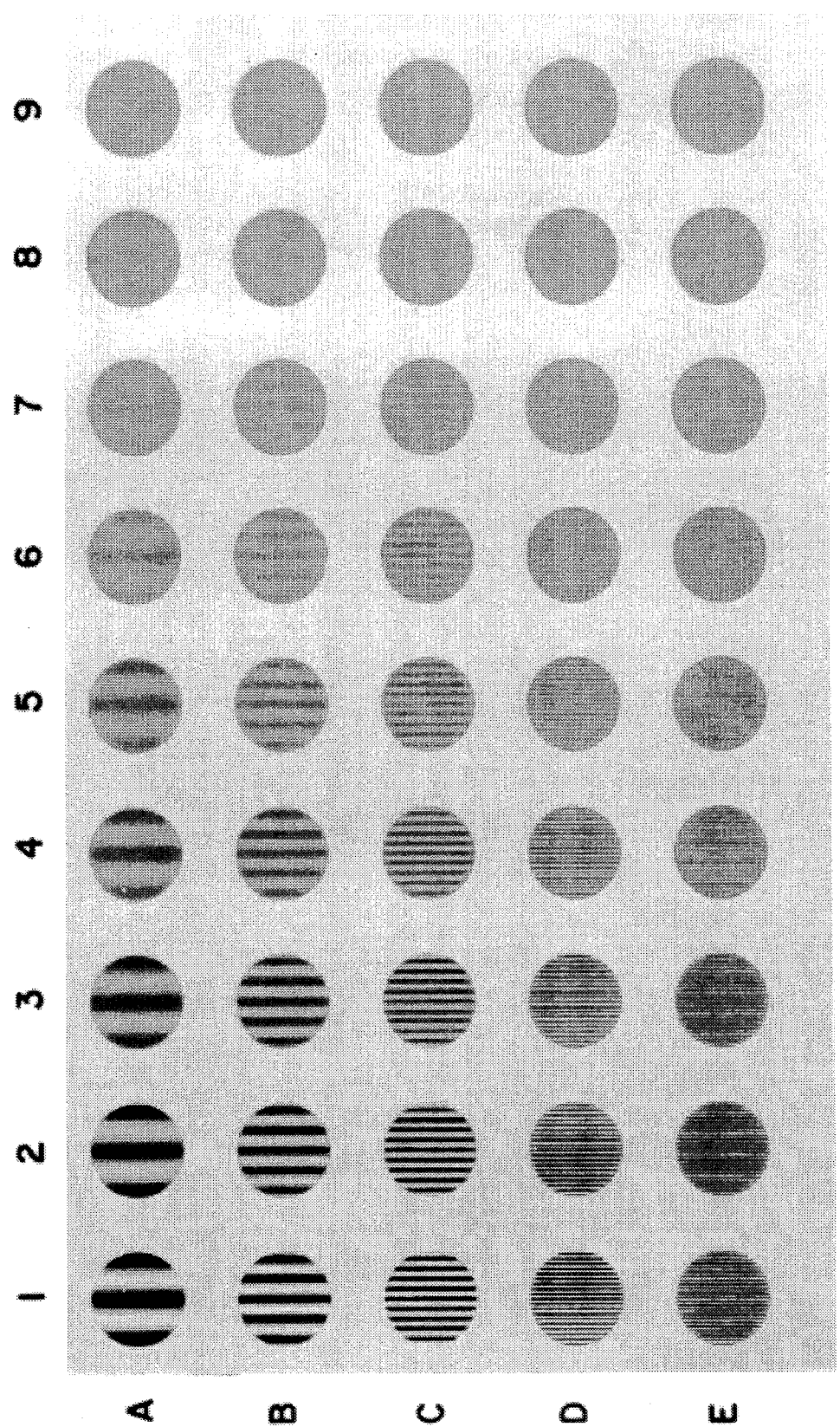
FIG._1. PRIOR ART

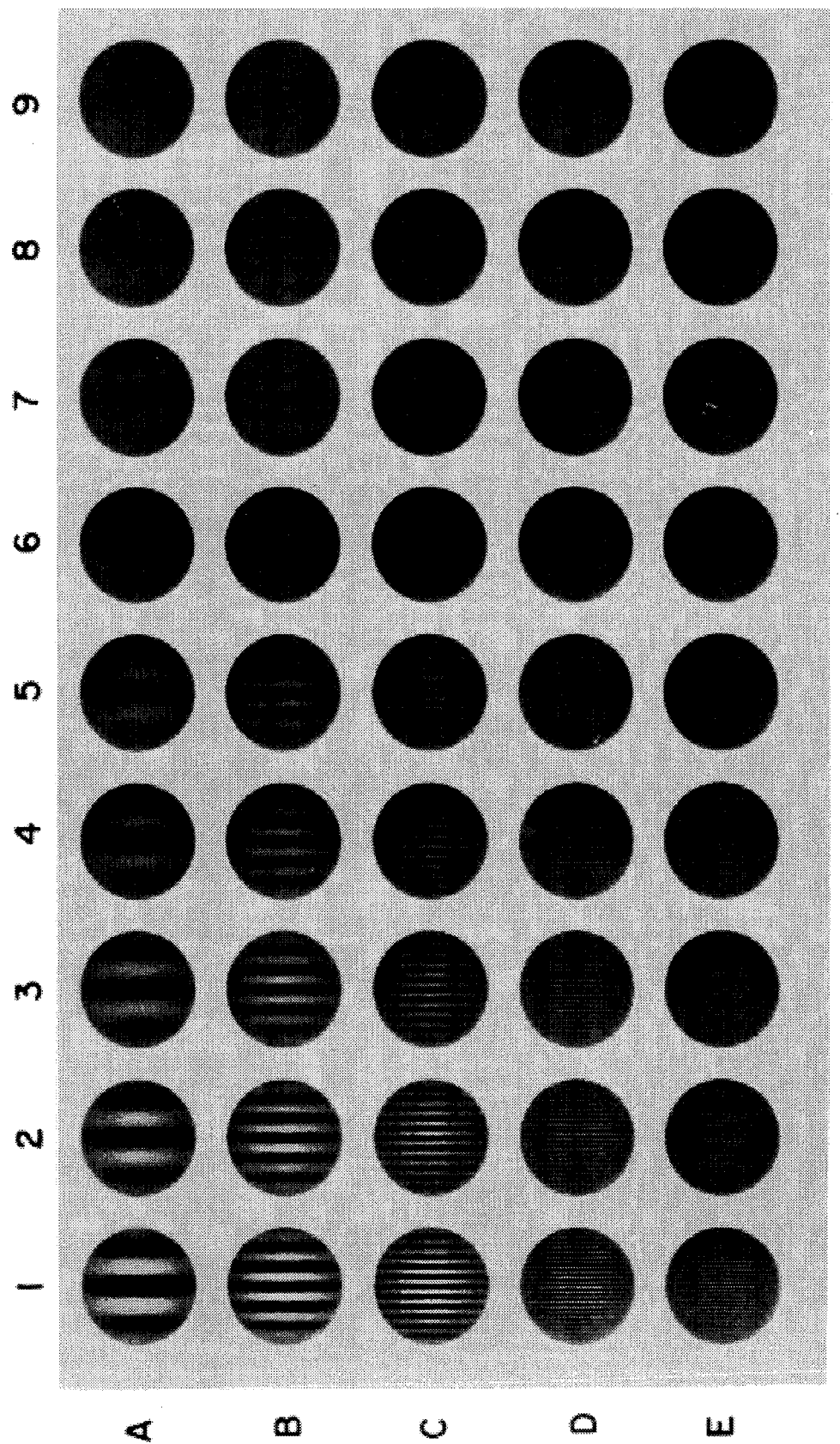
FIG._2. PRIOR ART

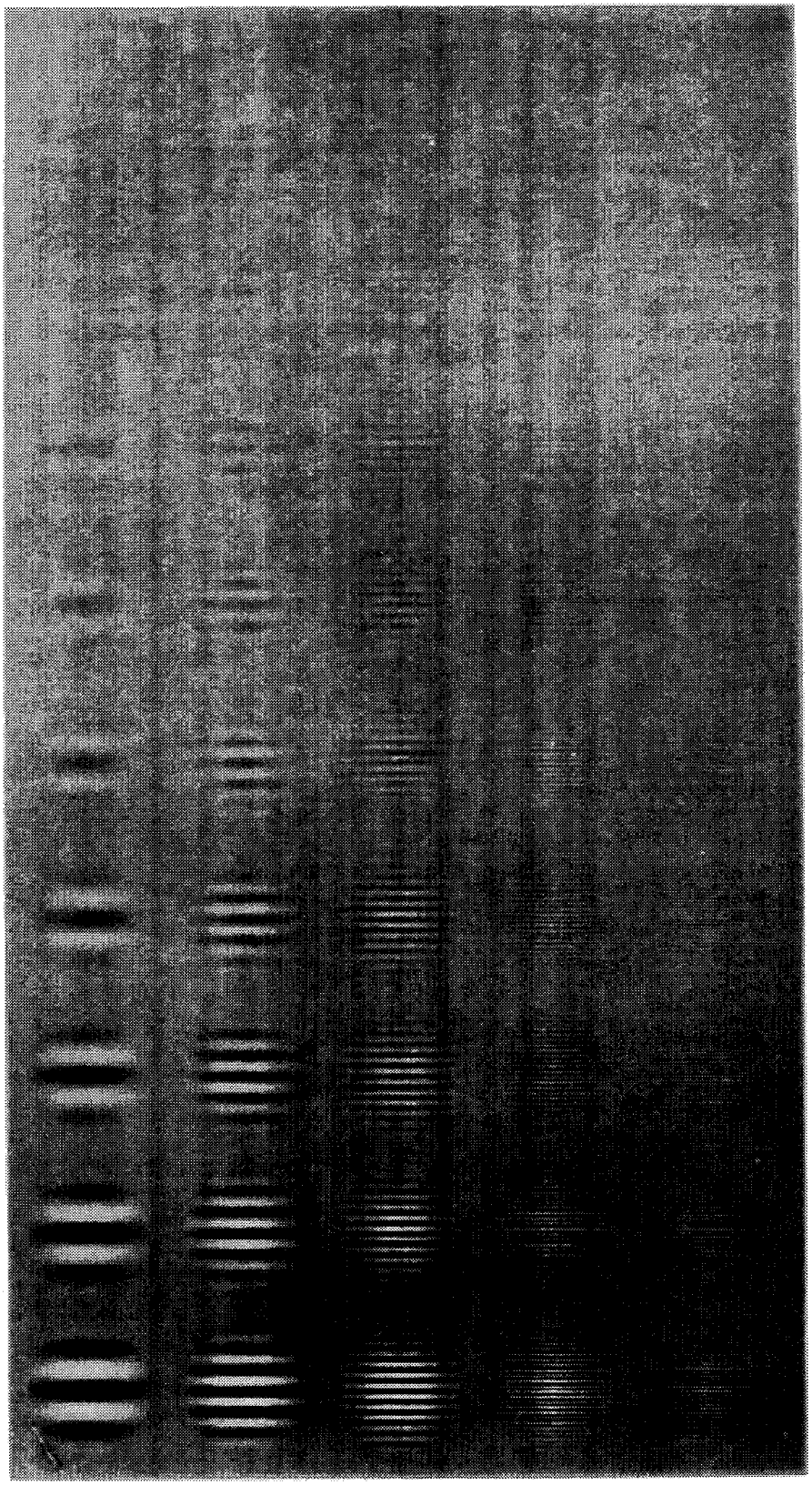
FIG._3.
PRIOR ART

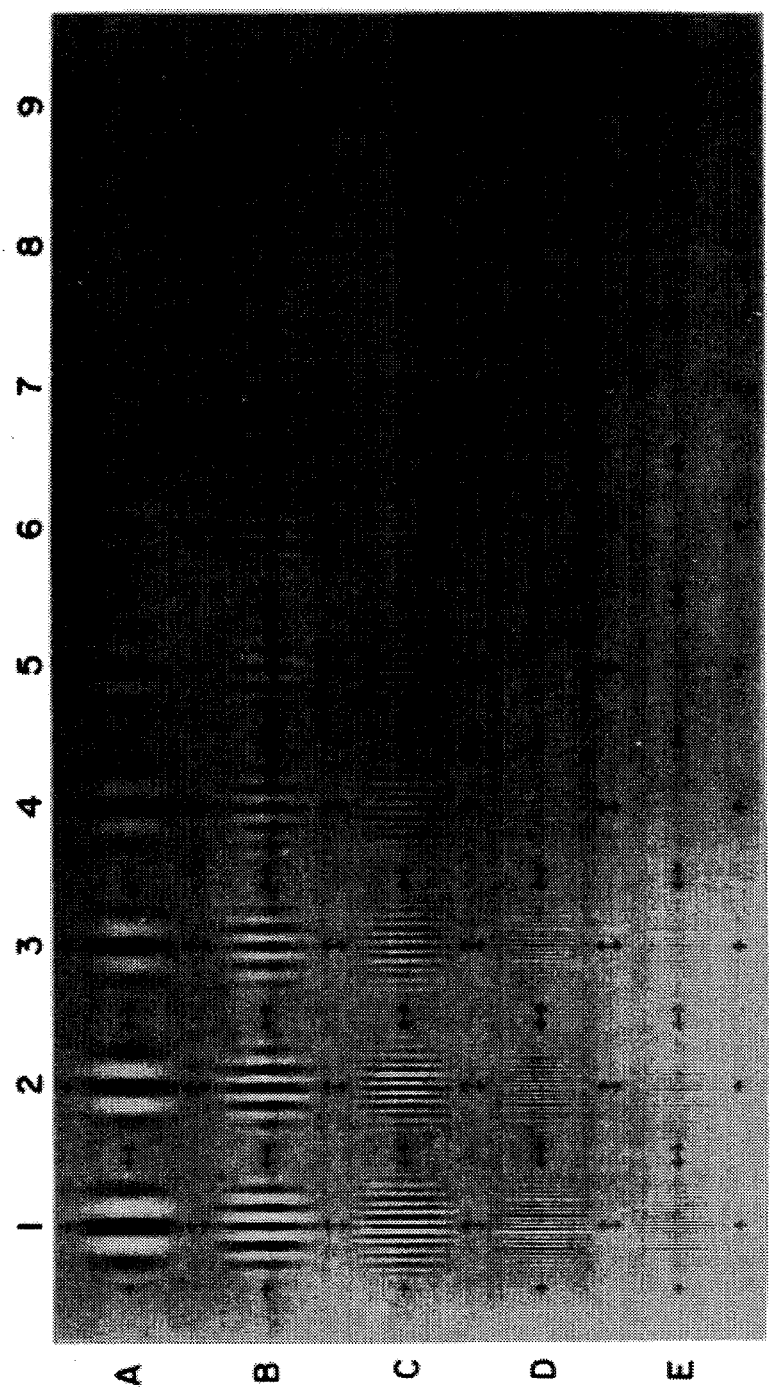
FIG._4.
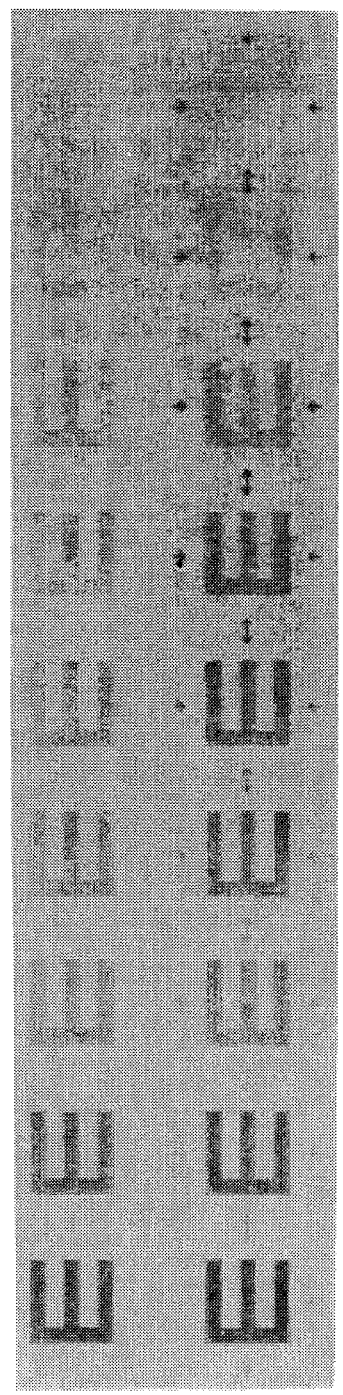
FIG._5.

SPATIAL FREQUENCY AND CONTRAST SENSITIVITY TEST CHART AND PROTOCOL

This is a Division of application Ser. No. 07/628,786 filed Dec. 17, 1990, now U.S. Pat. No. 5,414,479.

This invention is directed to a visual chart and a method of using that chart to evaluate the visual and/or imaging system undergoing analysis in terms of both contrast sensitivity and spatial response. Specifically, this invention is an improvement on my U.S. Pat. No. 4,365,873 entitled Spatial Frequency and Contrast Sensitivity Test Chart issued Dec. 28, 1982.

BACKGROUND OF THE INVENTION

There have been recently developed new protocols of vision test charts which test for the contrast perception of the subject or system being interrogated for visual contrast sensitivity and contrast acuity. An example of such a system is that disclosed in my U.S. Pat. No. 4,365,873 entitled Spatial Frequency and Contrast Sensitivity Test Chart issued Dec. 28, 1982. In the preferred embodiment in that patent, rows and columns of patches were presented against a white background. The gratings in successive rows of patches increase spatial frequency by octave steps. The patches in successive columns decrease contrast in half contrast increments. There results a system which enables measurement of contrast sensitivity and spatial frequency response.

This system has been the subject of criticism. It has been found by others that an aliasing artifact is present that appears to produce erroneous contrast sensitivity under conditions of high dioptic blur. It was suggested that the increased contrast sensitivity found at high spatial frequencies using +3 diopters of blur was due to the sharp edges and high luminance difference between the grating patches and the surround.

Aliasing, in this case, is said to be due to the interaction of the gratings with its own edges. The spatial frequency and contrast sensitivity test chart disclosed in my prior U.S. Pat. No. 4,365,873 uses small circular grating patches (about 1.4° of solid angle) with an average luminance considerably lower, about 20% of its surround. It has been suggested that because the high luminance grating stripes still have lower luminance than the surround, that the contrast of the grating surround is higher than that of the grating stripes. The resulting small circular grating can have beats that are more visible than the grating stripes. These beats have the same orientation as the true gratings. They can be used by the observer to produce a correct response even though the grating stripes may not be visible to that particular observer. It has been concluded that my spatial frequency and contrast sensitivity test chart ". . . seems unsuited to understanding the effects of blur on a patient's vision . . . . "

It is important to point out that the preceding criticisms will also apply to any other test charts comprised of targets having background mean luminance difference from the average of the test targets, especially those targets having sharp edges.

DISCOVERY OF THE PROBLEM

The spatial frequency and contrast sensitivity test chart of my prior U.S. Pat. No. 4,365,873 partially anticipated this problem in lines 23–31 of column 3. "Simply stated . . . Recognizing the potential biasing effects of an abrupt change in contrast between chart background and a luminance line at the edge of the patch, the contrast in each patch grate can be tapered to the background at a Gaussian rate. In the second instance, the background of the chart can be shaded into correspondence with the average contrast level of the patch encircled." I have investigated this aliasing problem. Patches for visual tests were developed as described above and are illustrated in this patent application in FIG. 3. Unfortunately, when the two steps suggested by me in my prior art patent are taken to ensure that they are present no aliasing artifacts, another more serious problem arises. This problem is that the Gaussian taper and mean luminance background produced in grating patches near the visual threshold cannot be located on the chart. Thus, when trying to determine the limits of visual sensitivity, those grating patches on the limits of visual sensitivity blend into the background and are difficult for the patient to physically locate on the chart. Stated in other terms, the patient is distracted into a search protocol which search protocol interferes with the simple contrast sensitivity test.

The imposition of a difficult target search task on top of the simple contrast sensitivity test frustrates the observer and increases test time. Additionally, I have found that it can produce erroneous results.

The reader will understand that discovery of a problem to be solved can constitute invention. The discovery set forth herein constitutes at least an important portion of this invention.

SUMMARY OF THE INVENTION

A method and apparatus for measuring and quantifying generalized visual sensitivity in terms of contrast sensitivity, spatial frequency response and eye brain recognition of image alignments or shapes is disclosed. A multiplicity of distinctly different information areas are provided, each of these information areas being generally delineated by indicia so as to eliminate patient or system search for an image and to generally designate the proximity of the information area for visual or system interrogation. The information areas may contain a grating having successive parallel aligned light and dark areas, which parallel aligned light and dark areas have a substantially linear character with the contrast levels and/or frequency of occurrence differing for different information areas. Each successive information area has a background with mean luminance being the average of that mean luminance found within the information area. Further, some information areas are provided with a taper at their edges, preferably a Gaussian taper, which taper imparts to the edges boundaries that blend into the mean luminance background. There results for images on the threshold of visual acuity information areas which only with careful examination can be discriminated from their backgrounds. As a result, indicia designating the general location of the information areas is required. Successive information areas can have either parallel aligned light and dark areas of differing angular orientation or can have an outline or shape of a readily recognizable object for identification by the patient or system being interrogated. There is thus presented a successive range of contrast and spatial frequency or size of the occurrence of successive information areas generally delineated by indicia to designate their location, these information areas upon observation by a person or system may be used as an accurate basis for determining the sensitivity and range of perception of that person or system to whom or to which the patterns are presented for viewing.

Other Objects, Features, and Advantages

This is the first time that indicia designating the general location of vision test targets has been required as a crucial component for the optimum development of contrast sensitivity charts. In order to get a true contrast measure of the visual target, uncorrupted by aliasing artifacts due to sharp luminance steps between the background and the test target and to be able to visually locate the target for inspection without concern for visual search capability, my research discloses three steps are required. First, an unsharp target edge smoothly blending into the background is required. Second, the background luminance must be the average luminance of the target. Third, indicia designating the general location of the information areas to be interrogated are required. These requirements are not only for threshold contrast testing using grating targets but also for the testing of other optotypes such as letters or Gaussian or other similar targets.

It will be recognized that in my previous apparatus and process, that it was not possible to impart to the successive information areas discernable shapes. In the present improvement, discernable shapes may be contained within the information areas for identification by the subject or system interrogated. These discernable shapes are virtually infinite in their possibility and can include anything from Snellen letter tests (such as E, F, L) to geometric shapes such as circles, squares, rectangles, triangles, animal outlines, faces, scenes, etc. The disclosed discernable shapes have the advantage of virtually eliminating random subject guessing of correct test responses as well as placing the eye-brain system in the more usual contrast and frequency discernment of real world objects. No longer is the disclosed system limited to choosing "alignments" from a limited vocabulary of possible alignments all in specifically identified interrogation zones.

The indicia designating the general location of the information area to be interrogated isolates the visual area for visual inspection. This indicia enables the low contrast targets to be brought within the central visual area of the eye, the most visually sensitive retinal region. This indicia enables good test/retest reliability, sensitivity and specificity. The indicia enable the target to be located and centrally fixated upon to produce reproducible testing results.

BRIEF DESCRIPTION OF THE DRAWINGS

Other objects, features and advantages of this invention will become more apparent after referring to the following specification and attached drawings in which FIG. 1 is a prior art eye chart which schematically depicts an embodying chart specifically designed to test human visual contrast sensitivity, with the gratings in successive rows of patches increased in spatial frequency by octave steps while successive columns decrease in contrast in half-contrast increments;

FIG. 2 is an illustration of the prior art incorporating the suggestion set forth in my prior art patent wherein a taper (here a Gaussian taper) is applied at the image edges;

FIG. 3 is the image of FIG. 2 placed against a background having the average mean luminance of the target area itself;

FIG. 4 is the invention herein, the invention including indicia designating the general location of the information areas to be interrogated; and FIG. 5 illustrates an embodiment of this invention in which shapes such as the shapes of the letter E are incorporated to the low contrast image of this invention to enable viewer recognition to fixate on ordinarily discernible and recognizable every day shapes.

Attention is now directed to FIG. 1 where one embodiment of the chart is schematically depicted. Each patch in FIG. 1 contains a calibrated grating whose luminance levels vary simultaneously between the peaks of luminance. The patches themselves are systematically organized over the face of the chart such that the columns have similar contrast levels while the rows have equal spatial frequency.

Referring to FIG. 2, and in recognition of the suggestion of my prior art patent, I provide a taper at the edge of my respective images to the background level. While any taper can be used, I prefer to use a taper at a Gaussian rate. Unfortunately, the prior art figure set forth in FIG. 2 is still subject to the aliasing artifact deficiency.

Referring to FIG. 3, the background of the chart is shaded into correspondence with the average contrast level of each patch. The viewer can readily see that the patches combine subtly with the background and the lower contrast patches become most difficult to locate.

With regard to the embodiment of FIG. 3, I have found that the resultant images require the subject under tests to hunt for their location. The superimposition of this hunting protocol on top of the subtle contrast testing complicates the test procedure. The patient tires easily. Results are not reproducible.

Further, although the target is generally oriented in a row and column designation, relating the areas to be examined to the rows and columns designated by the searcher becomes a tiring task. Error of area location follows.

Referring to FIG. 4, the invention herein is illustrated. Specifically, all areas subject to visual inspection by a subject or system under test are designated with indicia. The indicia generally delimits that area to be examined with the central retinal perception of the eye.

Referring to FIG. 5, an embodiment of this invention is disclosed in which the letter E is visually repeated. The reader will recognize that the single letter E could be substituted with additional letters. By way of example, such additional letters could include the letters E, L, F, T, etc.

It is important that the eye chart of my invention subtend a preferred solid angle from the human eye. This may be described in terms of the preferred dimensions of the visual sensitivity test chart targets as well as its preferred distance from the patient.

The embodying visual sensitivity test chart depicted in FIGS. 1–5 is approximately 61 cm (2 feet) high and approximately 91.5 cm (3 feet) wide. Each grating patch is 7 cm (2.75 inches) in diameter. The spatial frequencies covered by the chart range from 0.5 to 32 cycles per degree (CPD) (in one octave steps of 0.5, 1, 2, 4, 16, and 32 CPD). This extends from the first row of the illustrated chart to the last row. Those spatial frequencies in excess of 32 CPD could have been included in this chart, those frequencies are usually below the visual threshold under normal viewing conditions.

I prefer that my chart be viewed at a distance of 10 feet. This gives each area to be examined a solid angle of approximately 1.4 degrees.

It will be understood that the preferred dimensions above will admit various ranges. For example, a wide range of solid angles can be used. By way of an intermediate range, 1° to 3° may be used. Broadly, ranges anywhere from 0.5° to 180° can be utilized.

Distance likewise can be varied. Dependent upon the size of the chart utilized, 16 inches to 20 feet can separate the view from the chart or other visual presentation.

I set forth in my prior art patent a definition of contrast as a function of maximum and minimum luminance levels. This definition is incorporated by reference herein.

The level of contrast in the gratings of the embodying chart patches ranges from a maximum of approximately 15% to a lower bound of 0, progressing in half-contrast steps from a maximum at the left edge of the chart. A practical upper limit for contrast is 30%. Greater levels do not exercise or probe human visual contrast threshold faculty. In like manner the half-contrast steps are merely preferred increments. If a larger chart is deemed acceptable, increments such as those related by the square root of 2 are readily amenable.

In my prior art patent, the orientation of the striping of the patches was meaningful. In that patent I canted the shapes and orientations of the patches to interrogate the patient as to the direction of canting. Determination was made as to whether the patient properly recognized the patches.

Referring to FIG. 5, I include herewith another embodiment of my invention which includes the bounding indicia of my invention. The chart here shown includes a secession of repeating letters "E", which letters change in contrast from right to left across the chart. The letters change in their contrast level with respect to the background, the contrast level with respect to the background being uniform over the entire letter. The letters thus change from letters that are sharply delineated from their background on the left to letters fading into the background on the right. These letters are produced utilizing the grating technique previously discussed. As will be noted, the sharp contrast at the letters edge remains; it is only when this sharp contrast begins to fade with the fading of the entire letter into the background of the eye chart that the letter edges become difficult to see.

Again, indicia marking the location of the letters are used and indeed required. As the viewer can plainly see, when the letters approach the same contrast as the background (something which is personal for each viewer tested), location of the letters become increasingly difficult.

The letters have an additional advantage. In my prior art patent, I used a canting to the left, a canting to the right, as well as a vertical alignment. This was necessitated because I did not include discernable shapes. Unfortunately, with such canting of gratings, error can be introduced. By way of example, a patient can guess (being correct one time out of three) as to the direction of canting. Where the observer is operating on the limit of his own contrast sensitivity and vision, the ability of the patient to correctly guess can interfere with the reproducibility of the testing protocol disclosed. It is for that reason, that I offer the embodiment disclosed herein in FIG. 5.

Referring to FIG. 5, the reader will see the letter E reproduced. While I have used the same letter in the same alignment for ease of understanding, the reader will understand that differing letters with differing alignment are preferred.

I have used in this specification terms which make it clear that the test herein can either be one for determining human vision or, alternately, can test a system through which such imaging occurs. Such a system can include, by way of example, video presentations and the like.

Further, out of necessity, I have illustrated black and white photographs of a series of images, these images containing a photographic reproduction of the preferred dimension of the eye chart which I utilized.

The reader will understand that the reproduction of the images that I disclose should not be restricted to a purely visual chart presentation. By way of example, modern high-definition television systems could be used for the test herein disclosed. Further, the entire shape to be examined could be isolated on a screen. The shapes forming the subject matter of the test could be displayed on a screen in any order. Moreover, the mean background illumination could be varied from picture to picture. These and other changes may be made by those having skill in the art.

I have used the term "indicia" herein. This term should be considered in the broad sense. By way of example, it can include the preferred arrows. Alternately, it can include boarders. An example of boarders could include a video presentation of successive letters in which the patient under test was instructed to look in the same area of the surround for the letter. Naturally, boxes, circles and other regular boarders will likewise satisfy this definition of indicia. It is also possible to delineate by color or local luminance (either static or dynamic [flashing]) the area or section of the area to be examined. Broadly, anything that delineates the area to be examined and does away with the distracting hunting will satisfy this requirement of my invention.

What is claimed is:

1. Vision sensitivity evaluation apparatus including:

means for presenting a perceivable multiplicity of distinctly separated information areas;

each of said information areas comprising successively dimmer regions between successive edges of said information areas, the regions of which have a substantially linear character and the contrast level and/or spatial frequencies or size of occurrence of which differ in different information areas;

the edges of each information area successively tapered in said contrast level and/or frequency and/or size of occurrence to approach the level of a surround;

the surround of said information areas having a value of mean luminance which tapers to the mean luminance of the information area being interrogated;

indicia immediate the boundary of the location of each information area against said surround for indicating to the subject or system being tested the location of the information area for interrogation; and whereby successive information areas are presented in a range of contrasting luminance and spatial frequency or size of occurrence therein of the light and dark regions which upon observation by a person or system may be used as an accurate basis for determining the sensitivity and range of perception.

2. Vision sensitivity evaluation apparatus including:

means for presenting a perceivable multiplicity of distinctly separated information areas;

each of said information areas employing successively alternated dimmer regions between successive edges of said information areas, the regions of which have a substantially linear character and the contrast level and/or spatial frequencies or size of occurrence of which differ in different information areas;

the edges of said information areas terminating at boundaries of distinctly recognizable shapes for identification by a subject or system being tested;

the surround of said information area having a value of mean luminance;

each information area having a value of mean luminance which varies successively varies in contrast to the value of mean luminance of the surround from values readily discernible from the value of the surround;

indicia immediate the boundary of the location of each information area against said surround for indicating to the subject or system being tested the location of the information area for interrogation; and whereby successive information areas are presented in a range of contrasting luminance and spatial frequency or size of occurrence therein of the light and dark regions which upon observation by a person or system may be used as an accurate basis for determining the sensitivity and range of perception.

* * * * *